United States Patent
Bobo, Sr. et al.

(10) Patent No.: US 10,687,720 B2
(45) Date of Patent: Jun. 23, 2020

(54) AUTOMATIC AIR MANAGEMENT SYSTEM

(71) Applicant: IRRAS USA, INC., San Diego, CA (US)

(72) Inventors: Donald E. Bobo, Sr., Fountain Valley, CA (US); David Robbins Asbury, Lake Elsinore, CA (US)

(73) Assignee: IRRAS USA, INC., San Diego, CA (US)

( * ) Notice: Subject to any disclaimer, the term of this patent is extended or adjusted under 35 U.S.C. 154(b) by 115 days.

(21) Appl. No.: 14/734,947

(22) Filed: Jun. 9, 2015

(65) Prior Publication Data

US 2015/0351649 A1  Dec. 10, 2015

Related U.S. Application Data

(60) Provisional application No. 62/009,874, filed on Jun. 9, 2014.

(51) Int. Cl.
*A61B 5/03* (2006.01)
*A61B 5/00* (2006.01)
*A61M 25/00* (2006.01)

(52) U.S. Cl.
CPC .............. *A61B 5/036* (2013.01); *A61B 5/031* (2013.01); *A61B 5/6852* (2013.01); *A61M 25/0097* (2013.01); *A61M 2025/0002* (2013.01); *A61M 2205/3331* (2013.01); *A61M 2205/3337* (2013.01); *A61M 2210/0687* (2013.01)

(58) Field of Classification Search
None
See application file for complete search history.

(56) References Cited

U.S. PATENT DOCUMENTS

| | | |
|---|---|---|
| 2,866,453 A | 12/1958 | Jewett |
| 3,122,136 A | 2/1964 | Murphy, Jr. |
| 3,662,743 A | 5/1972 | Amarante et al. |

(Continued)

FOREIGN PATENT DOCUMENTS

| | | |
|---|---|---|
| EP | 0846472 A1 | 6/1998 |
| EP | 0972535 A2 | 1/2000 |

(Continued)

OTHER PUBLICATIONS

WIPO, U.S. International Search Authority, International Search Report and Written Opinion dated Sep. 1, 2015 in International Patent Application No. PCT/US2015/034950, 7 pages.

(Continued)

*Primary Examiner* — Sean P Dougherty
*Assistant Examiner* — Benjamin S Melhus
(74) *Attorney, Agent, or Firm* — Inskeep IP Group, Inc.

(57) ABSTRACT

A powered or automatic air management system for measuring pressure from an air pressure catheter located within a patient. Powered pumps are included in a remote pump assembly to automatically adjust the air volume to a desired level. A pressure transducer assembly is located at the bed of the patient and is connected to an air catheter, and a separate pump assembly is fixed to an IV pole away from the patient and connected to a pressure monitor to display the pressure readings. By locating the pressure transducer to a location relatively close to the connection point of the catheter, more accurate pressure readings can be achieved.

8 Claims, 17 Drawing Sheets

(56) References Cited

U.S. PATENT DOCUMENTS

| | | | |
|---|---|---|---|
| 3,714,869 A | 2/1973 | Flory et al. | |
| 3,719,070 A | 3/1973 | Hanes | |
| 3,884,242 A | 5/1975 | Bazell et al. | |
| 4,077,394 A | 3/1978 | McCurdy | |
| 4,301,811 A | 11/1981 | Layton | |
| 4,714,461 A | 12/1987 | Gabel | |
| 4,776,347 A | 10/1988 | Matthews | |
| 4,901,735 A | 2/1990 | von Berg | |
| 4,903,707 A | 2/1990 | Knute et al. | |
| 4,934,375 A | 6/1990 | Cole et al. | |
| 5,562,614 A | 10/1996 | O'Donnell | |
| 5,573,007 A | 11/1996 | Bobo, Sr. | |
| 5,644,285 A | 7/1997 | Maurer | |
| 5,810,741 A | 9/1998 | Essen-Moller | |
| 5,984,879 A | 11/1999 | Wallace et al. | |
| 6,056,697 A | 5/2000 | Owens et al. | |
| 6,070,855 A | 6/2000 | Chuang et al. | |
| 6,231,524 B1 | 5/2001 | Wallace et al. | |
| 6,447,462 B1 | 9/2002 | Wallace et al. | |
| 7,654,967 B2 | 2/2010 | Bobo, Sr. | |
| 7,780,679 B2 | 8/2010 | Bobo, Sr. et al. | |
| 8,360,988 B2 | 1/2013 | Bobo, Sr. et al. | |
| 2002/0151854 A1 | 10/2002 | Duchon et al. | |
| 2003/0028074 A1* | 2/2003 | Tracey | A61B 1/32 600/29 |
| 2007/0060834 A1* | 3/2007 | Odland | A61B 5/0215 600/561 |
| 2007/0112279 A1* | 5/2007 | Iseberg | A61B 5/03 600/559 |
| 2007/0191678 A1* | 8/2007 | Sekiguchi | A61B 1/00082 600/116 |
| 2008/0077043 A1* | 3/2008 | Malbrain | A61B 5/036 600/547 |
| 2008/0077078 A1* | 3/2008 | Locke | A61M 1/0025 604/35 |
| 2009/0221933 A1* | 9/2009 | Nishtala | A61B 5/205 600/561 |
| 2010/0113968 A1* | 5/2010 | Bobo, Sr. | A61B 5/031 600/561 |
| 2010/0241132 A1 | 9/2010 | Bobo, Sr. et al. | |
| 2011/0313394 A1 | 12/2011 | Bobo, Sr. | |
| 2012/0283630 A1 | 11/2012 | Lee et al. | |
| 2013/0231584 A1* | 9/2013 | Burnett | A61B 5/036 600/561 |
| 2013/0345595 A1 | 12/2013 | Bobo, Sr. et al. | |
| 2016/0029941 A1* | 2/2016 | Jensen | G01L 19/0023 600/561 |

FOREIGN PATENT DOCUMENTS

| | | |
|---|---|---|
| EP | 2 349 433 A1 | 8/2011 |
| GB | 968376 A | 9/1964 |
| GB | 2318513 A | 4/1998 |
| WO | WO 2010048638 A1 | 4/2010 |

OTHER PUBLICATIONS

United States Patent and Trademark Office, Notice of Allowance dated Jun. 30, 2014 in U.S. Appl. No. 13/752,079, 5 pages.

United States Patent and Trademark Office, Office Action dated Dec. 13, 2013 in U.S. Appl. No. 13/752,079, 10 pages.

United States Patent and Trademark Office, Notice of Allowance dated Sep. 19, 2012 in U.S. Appl. No. 12/606,169, 5 pages.

United States Patent and Trademark Office, Final Office Action dated Jan. 10, 2012 in U.S. Appl. No. 12/606,169, 11 pages.

United States Patent and Trademark Office, Office Action dated Jul. 26, 2011 in U.S. Appl. No. 12/606,169, 10 pages.

European Patent Office, Examination Report dated Jun. 20, 2011 in European Patent Application No. 09822858.8-1257, 2 pages.

WIPO, U.S. International Preliminary Examining Authority, International Preliminary Report on Patentability dated May 5, 2011 in International Patent Application No. PCT/US2009/062132, 7 pages.

United States Patent and Trademark Office, Office Action dated Mar. 11, 2011 in U.S. Appl. No. 12/606,169, 13 pages.

WIPO, U.S. International Search Authority, International Search Report and Written Opinion dated Dec. 15, 2009 in International Patent Application No. PCT/US2009/062132, 8 pages.

\* cited by examiner

AUTOMATIC AIR MANAGEMENT SYSTEM

RELATED APPLICATIONS

This application claims priority to U.S. Provisional Application Ser. No. 62/009,874 filed Jun. 9, 2014 entitled Automatic Air Management System, which is hereby incorporated herein by reference in its entirety.

BACKGROUND OF THE INVENTION

Presently, biologically compatible air-based pressure monitoring catheters are used in a number of medical applications to monitor pressure at various locations within a mammalian body. For example, air-based pressure monitoring catheters may be inserted into the skull of a patient thereby permitting the external monitoring of intra-cranial pressure.

Currently, a number of air-based pressure monitoring catheters have been developed. Generally, these air-based pressure monitoring catheters comprise a catheter having an air lumen formed therein which communicates with a bladder positioned at or near its distal end. In addition, the catheter includes a connector located at or near its proximal end which may be connected to an external pressure transducer. During use, the volume of the bladder attached to the catheter changes as pressure varies in accordance with Boyle's Law ($P_1V_1=P_2V_2$). As a result, the pressure of the gas within the catheter becomes equal to that of the environment surrounding the bladder. The media surrounding the bladder must be capable of movement to accommodate the variations in bladder volume as pressure changes.

The use of air-based pressure monitoring catheters in low or negatively pressurized environments has proven problematic. When the proximal connector is open to atmospheric pressure in the process of periodically replacing air lost by diffusion through the bladder, the external pressure extant in the body site monitored on a bladder will expel residual air from the bladder. If the pressure is low or negative, a significant amount of residual air may remain in the bladder. The amount of air injected is intended to be sufficient to keep the bladder in an active state. If this volume is added to the residual air in a bladder that has not been completely collapsed by the environment around it, the sum of the residual air and injected air exceed the intrinsic volume of a fully shaped bladder. Should this happen, a positive pressure is established in the bladder. The bladder is now unable to read pressure below the internal pressure created.

Air management systems such as those seen in U.S. Pub. No. 2007/0208270, U.S. Pat. Nos. 6,447,462, 8,876,729, and 8,360,988 which are all herein incorporated by reference, allow a user to adjust the amount of air in a system. For example, these systems allow a user to vent the air passage of the catheter to the open environment, then charge the passage with an amount of air. This allows a proper, known volume of air to be located in the system, thereby allowing the system to accurately calculate pressure within a patient's body.

SUMMARY OF THE INVENTION

One embodiment is generally directed to a powered or automatic air management system for measuring pressure from an air pressure catheter located within a patient. While prior art air management systems, such as those in U.S. Pat. No. 8,360,988, require a user to manually charge the pressure system with a known volume of air (i.e., by moving a piston by hand), the present embodiment includes powered pumps to automatically adjust the air volume to a desired level. Additionally, while prior systems include the system's pressure transducer, manual pumps, and other components in a single enclosure, the present embodiment includes a pressure transducer assembly that is located at the bed of the patient and a separate pump assembly that is fixed to an IV pole away from the patient and connected to a pressure monitor to display the pressure readings. By locating the pressure transducer to a location relatively close to the connection point of the catheter, more accurate pressure readings can be achieved. Additionally, the weight of the pump mechanism is located on the IV pole, allowing the components near the patient to be relatively lightweight.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
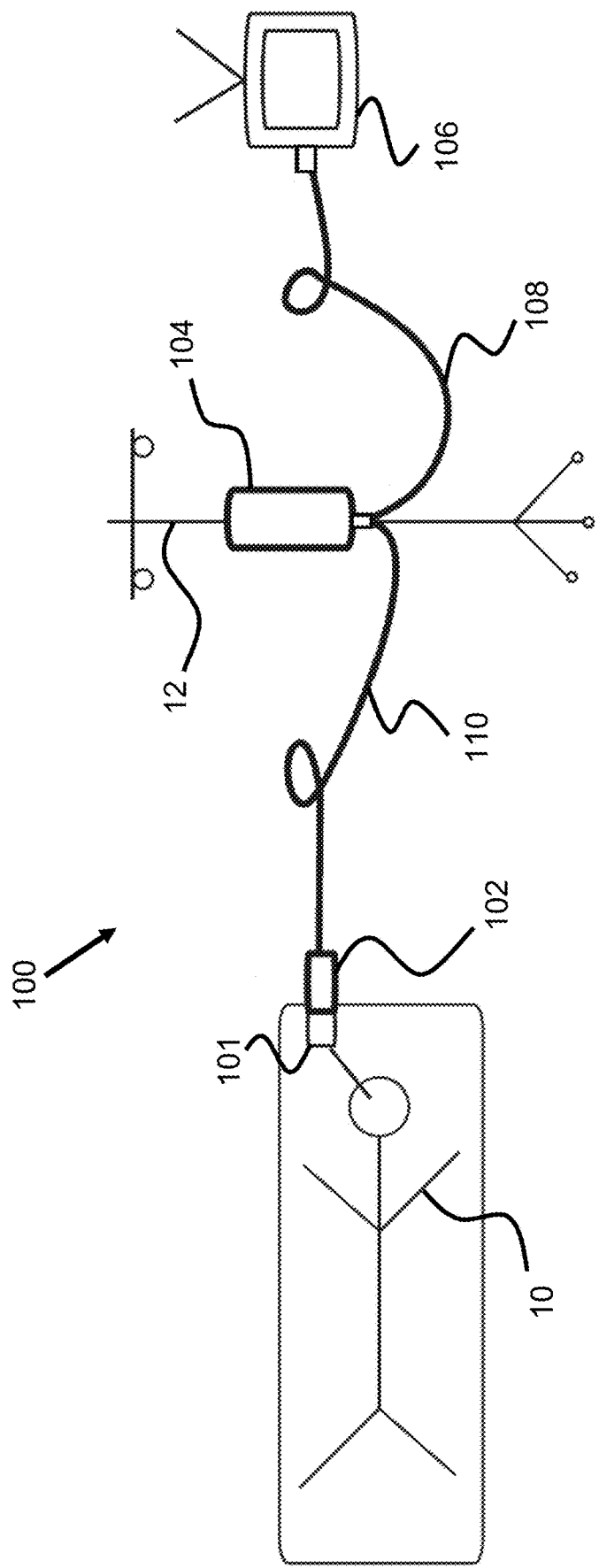
FIG. 1 is an overview of an automatic air management system for pressure measurement with an air catheter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is generally directed to a powered or automatic air management system 100, as seen in FIG. 1, for measuring pressure from an air pressure catheter 101 located within a patient 10. While prior art air management systems, such as those in U.S. Pat. No. 8,360,988, require a user to manually charge the pressure system with a known volume of air (i.e., by moving a piston by hand), the present embodiment includes powered pumps to automatically adjust the air volume to a desired level. Additionally, while prior systems include the system's pressure transducer, manual pumps, and other components in a single enclosure, the present embodiment includes a pressure transducer assembly 102 that is located at the bed of the patient and a separate pump assembly 104 that is fixed to an IV pole 12 that is away from the patient (e.g., 6 feet) and connected to a pressure monitor 106 (e.g., 10 feet maximum from the patient) to display the pressure readings. By locating the pressure transducer to a location relatively close to the connection point of the catheter, more accurate pressure readings can be achieved.

It should be noted that the present automatic air management system 100 can be used in connection with measuring pressure at any location within a human body, it is especially useful for measuring intracranial pressure (ICP), which is often measured in connection with treatment of traumatic brain injury.

Figure 2:
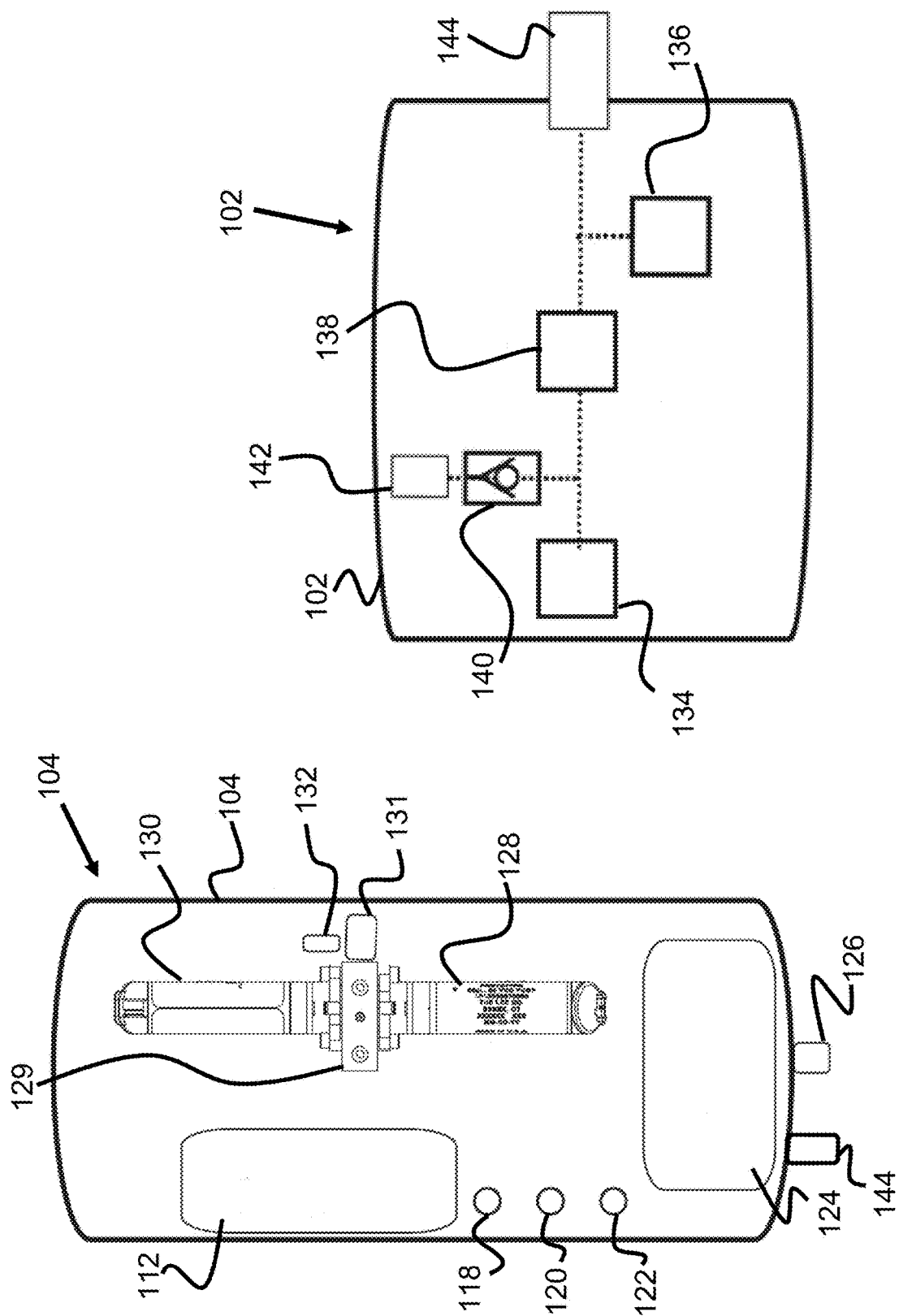
FIGS. 2 and 3 illustrate a pump assembly and a pressure transducer assembly of the system of FIG. 1.
Figure 3:
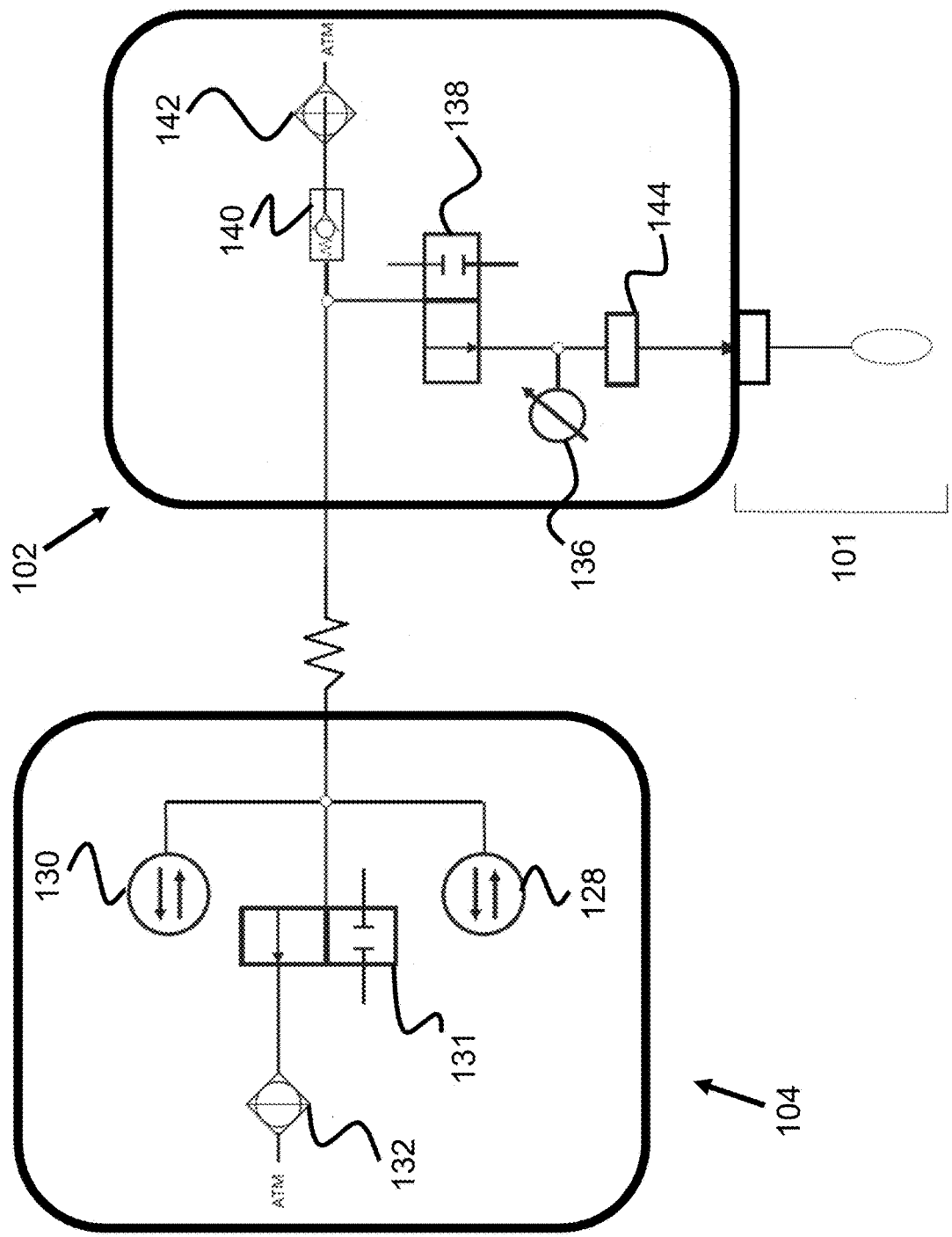

One embodiment of the pump assembly 104 and the pressure transducer assembly 102 are illustrated in FIG. 2 (general overview) and FIG. 3 (schematic view of the system's air passage). The air passage of the system is represented by the connecting lines in FIG. 3, of which various components are connected. The pump assembly 104 includes two solenoid pumps 128 and 130 (e.g., 50 μL pumps) connected to the passage, as well as a pump assembly valve 131 and a filter 132. The valve 131 opens or closes the passage from opening to the atmosphere through the filter 132, while the pumps 128 and 130 are connected to the air passage on the opposite side of the valve 131.

Figure 4:
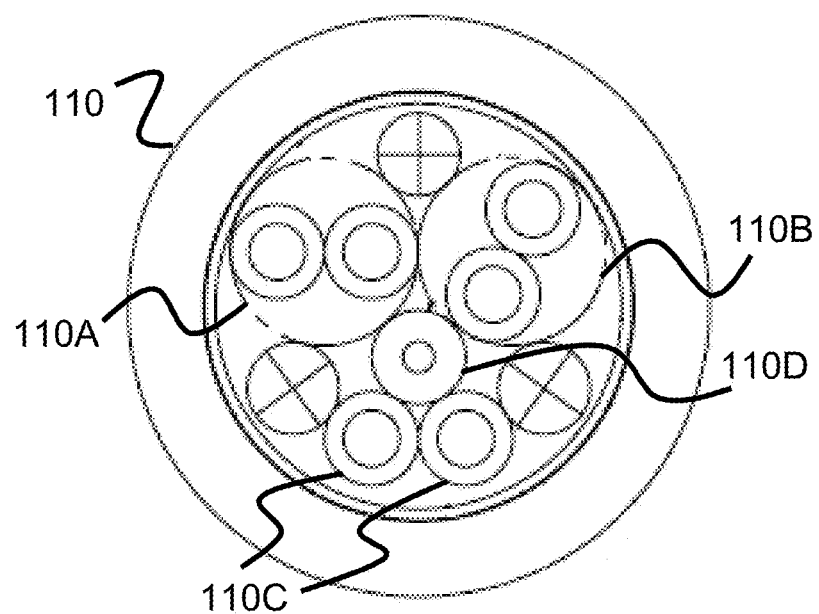
FIG. 4 illustrates a cross section of a pressure transducer assembly cable.

The air passage further connects to the pump connector socket 126, which contains pneumatic and electrical connections that connect to the transducer assembly cable 110. One specific example of the layout of the transducer assembly cable 110 can be seen in FIG. 4. Cables 110A are an electrical conduit that provide power from the pump assembly 104 to the pressure transducer assembly 102, Cables 110B transmit the pressure signal from the pressure transducer 136 to the pump assembly 104, cables 110C provide power from the pump assembly 104 to the valve 138, and pneumatic conduit 110D provides a pneumatic connection from the pump assembly 104 to the pressure transducer assembly 102.

The transducer assembly cable 110 connects to the transducer assembly 102 via connector 134. As seen in FIGS. 2 and 3, the air passage initially splits off to connect to a check valve 140 that vents to atmosphere via filter 142. The passage also connects to a valve 138 that opens or closes the air passage at that location. On the other side of the valve 138, the air passage connects to a pressure transducer 136 and to the catheter connector 144. Finally the air catheter 101 connects to the connector 144, allowing the air passage to connect to the air passage and air bladder within the catheter 101.

The operation of the components of both the pressure transducer assembly 102 and the pump assembly 104 are preferably controller by a control assembly, which are preferably components on a printed circuit board 112. For example, the printed circuit board 112 may include a microprocessor that executes firmware and/or software stored in a memory that, when executed, performs the functions described in this specification. The circuit board 112 may also be connected to "zero monitor" button 118 to allow a user to zero out the pressure signal to the monitor 106, a "prime system" button 120 that allows a user to inject the desired amount of air into the system, and a "stop" button 24 that allows a user to stop the pump assembly 104. While not shown in FIGS. 2 and 3, an alarm LED and an "alarm pause" button can also be included, which indicate a problem with the system and provide a mechanism to stop the alarm, respectively, in such a situation.

Figure 5:
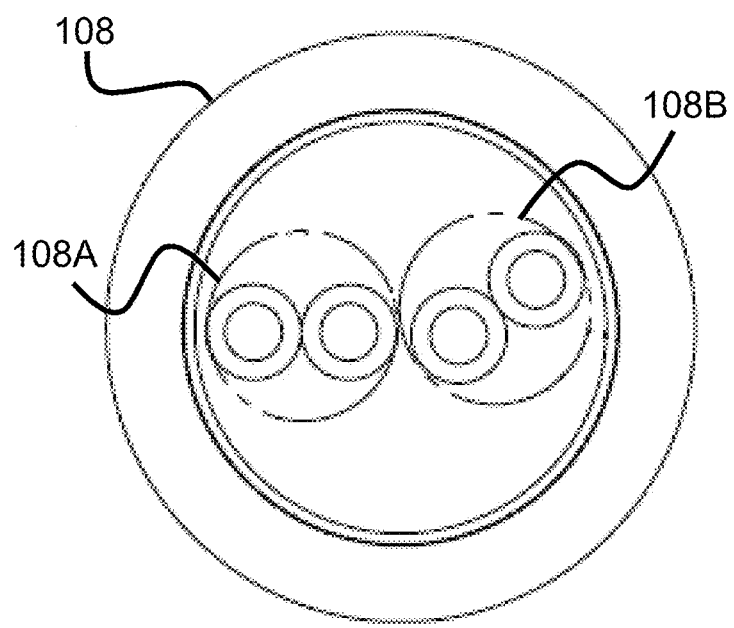
FIG. 5 illustrates a cross section of a pressure monitor cable.

Further, the circuit board 112 is connected to monitor connector socket 144 that connects with the pressure monitor cord 108 so as to communicate with the monitor 106 (e.g., via one of the electrical conduits 108A or 108B in FIG. 5), to a battery 124 via connector 116 to power the system, to the solenoid pumps 128 and 130, the valves 138, and to the transducer 136, to control pressure within the system and provide pressure measurement, respectively. With regard to the electrical conduits 108A and 108B, the patient monitor excitation on these conduits wakes up the system 100 for operation and sends voltage to the pressure transducer assembly 102 and receives the pressure signal from the transducer assembly 102.

It should be noted that the automatic air management system 100 and the catheter 101 must have, not only a known amount of air, but an amount that does not over or under inflate the air bladder of the catheter 101. For example, if the system is over inflated, the resulting pressure readings will be greater than the pressure external to the catheter within the patient's body (e.g., intracranial pressure). If the system is under inflated, the pressure within the catheter 101 will read less than that within the patient's body, especially with high pressures in the patient.

In the present embodiment, the pressure within the system 100 is maintained via three main pump cycles. The first is the evacuation cycle in which the valve 138 is opened and the solenoid pumps 128 and 130 displace volume within the air passage (e.g., by 100 μL), thereby pulling residual air from the air passage of the catheter 101. The valve 138 is then closed, sealing off the air passage within the catheter 101.

The second cycle is the injection cycle, in which the valve 138 is again opened and the solenoid pumps 128 and 130 are again actuated to displace volume within the air passage (e.g., by 100 μL), thereby pulling more residual air from the air passage of the catheter 101. This lowers the pressure within the air passage to a negative pressure equal to the crack pressure of the check valve 140 (e.g., 4 kPa). Next, the solenoid pumps 128 and 130 again displace volume so as to decrease the system volume (e.g., by 100 μL), thereby increasing the amount of air in the catheter 101.

The third cycle is the air optimization cycle, in which a decision point occurs. If the pressure is above a predetermined level (e.g., 40-60 mmHg or greater), the valve 138 closes. If the pressure is less than a predetermined level (e.g., 40-60 mmHg or less), one of the solenoid pumps 128 or 130 displaces volume (e.g., by 50 μL), increasing the system volume, and removing air from the system. The valve 138 then closes and there pressure transducer 136 begins monitoring the pressure.

As seen with regard to the air optimization cycle described above, having two solenoid pumps 128 and 130 allows more granularity when inflating and deflating the air bladder of the catheter 101. This can allows the system to better compensate for dilating in low pressure environments or high pressure environments without adding or extracting excessive volumes of air. Hence, the optimal amount of air can be present within the bladder of the catheter 101 at any pressure.

In another aspect of the present invention, the software executed by the microprocessor can detect connection and disconnection of the catheter 101 from the pressure transducer assembly 102. For example, if the transducer 136 detects a positive pressure spike, the catheter may have been recently connected. If the transducer 136 detects a negative pressure spike, the catheter may have been disconnected. This detection may also result in an indicator on either the pump assembly 104 or the transducer assembly 102 indicating either state to the user (e.g., via a changing color or flashing of an LED). Alternately, the catheter detection can be achieved by an optical sensor, mechanical switch, or an electromechanical sensor (e.g., a Halls-effect sensor).

Figure 6A:
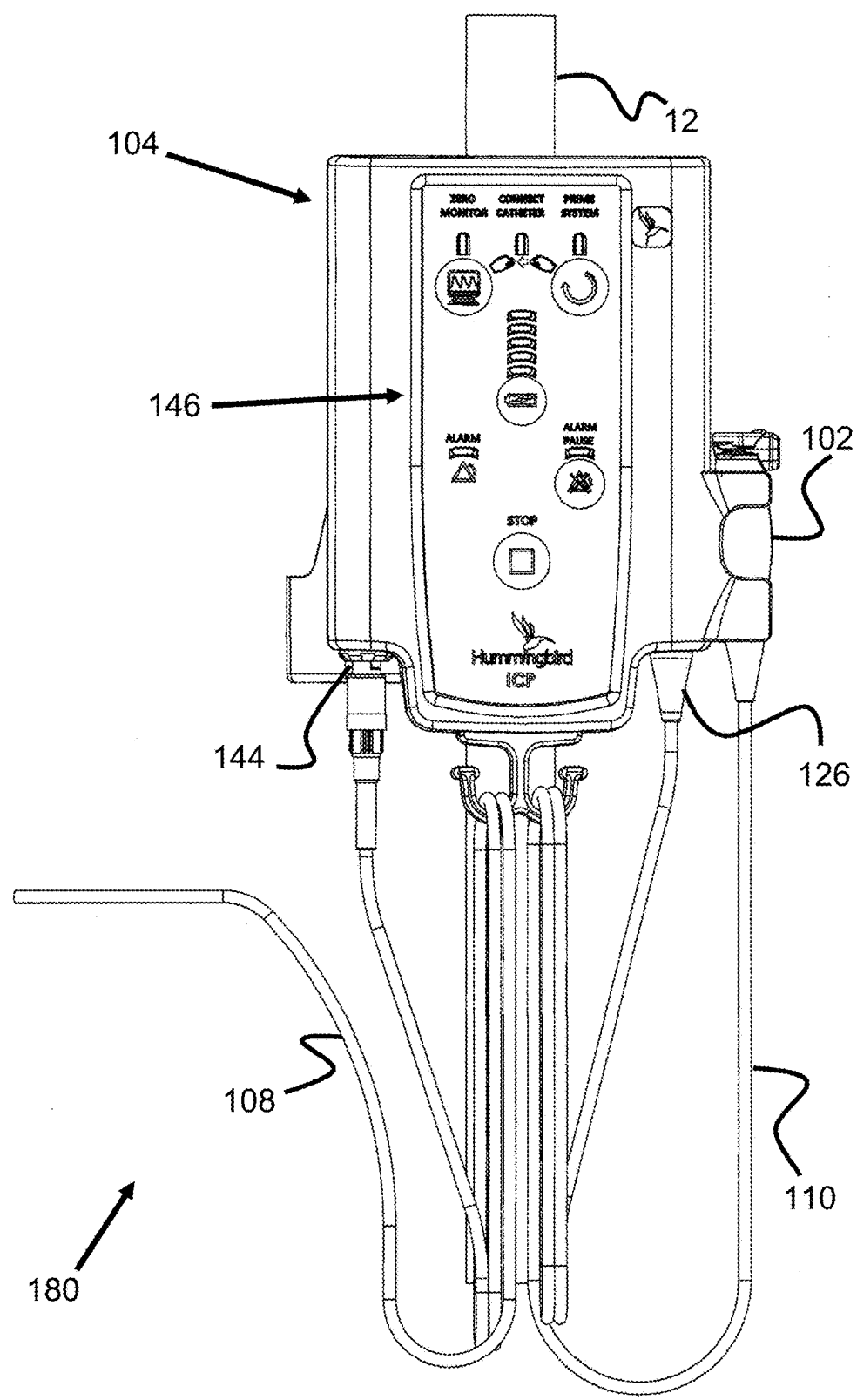
FIG. 6A-8 illustrate various aspects of an exterior of another embodiment of a pump assembly.
Figure 6B:
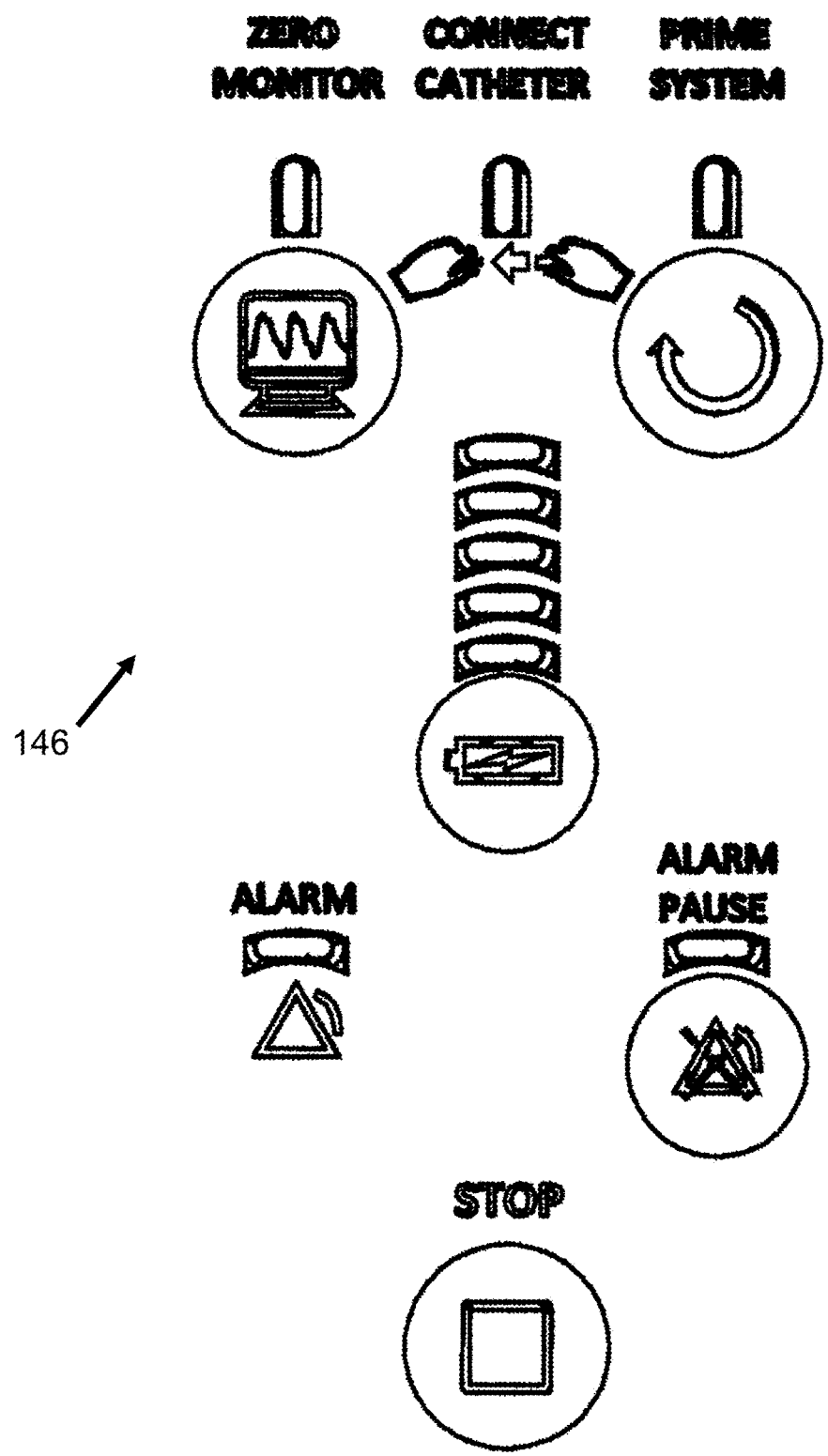

FIGS. 6A-23 illustrate various aspects of another embodiment of an automatic air management system 180 that is generally similar to the previously described embodiment 100. Turning first to FIGS. 6A and 6B, the pump assembly 104 includes a user interface 146, a monitor connector 144, and a transducer assembly connector 126. This pump assembly 104 can be fixed to and removed from an I.V. pole 12.

FIG. 6B illustrates an enlarged view of the user interface 146 that indicates and performs various functions and aspects of the system 180. Specifically, a "Zero Monitor" LED indicator and button causes the pump to zero out the monitor 106 prior to use, ensuring an accurate pressure will be displayed. Next, a "Connect Catheter" LED indicator indicates whether the catheter 101 is connected to the pressure transducer assembly 102. This connection status can be sensed via a pressure measurement (e.g., the pressure is equal to the outside atmosphere) or via a mechanical mechanism on the transducer assembly 102 (e.g., a button or switch). A "Prime System" LED indicator and button allows the user to activate the pump assembly 104 to inject the desired amount of air into the air passage and catheter 101, so that pressure measurement can take place. A battery indicator is also shown, indicating an estimated battery level (e.g., via a plurality of vertical LEDs). Next, an "Alarm" LED indicator and "Alarm Pause" button indicate to the user that problem exists with the system, such as the pressure measurement is out of normal range or that the battery is critically low, and that such an alarm can be temporarily paused. Finally, a "Stop" button stops operation of the pump assembly 104.

Figure 7:
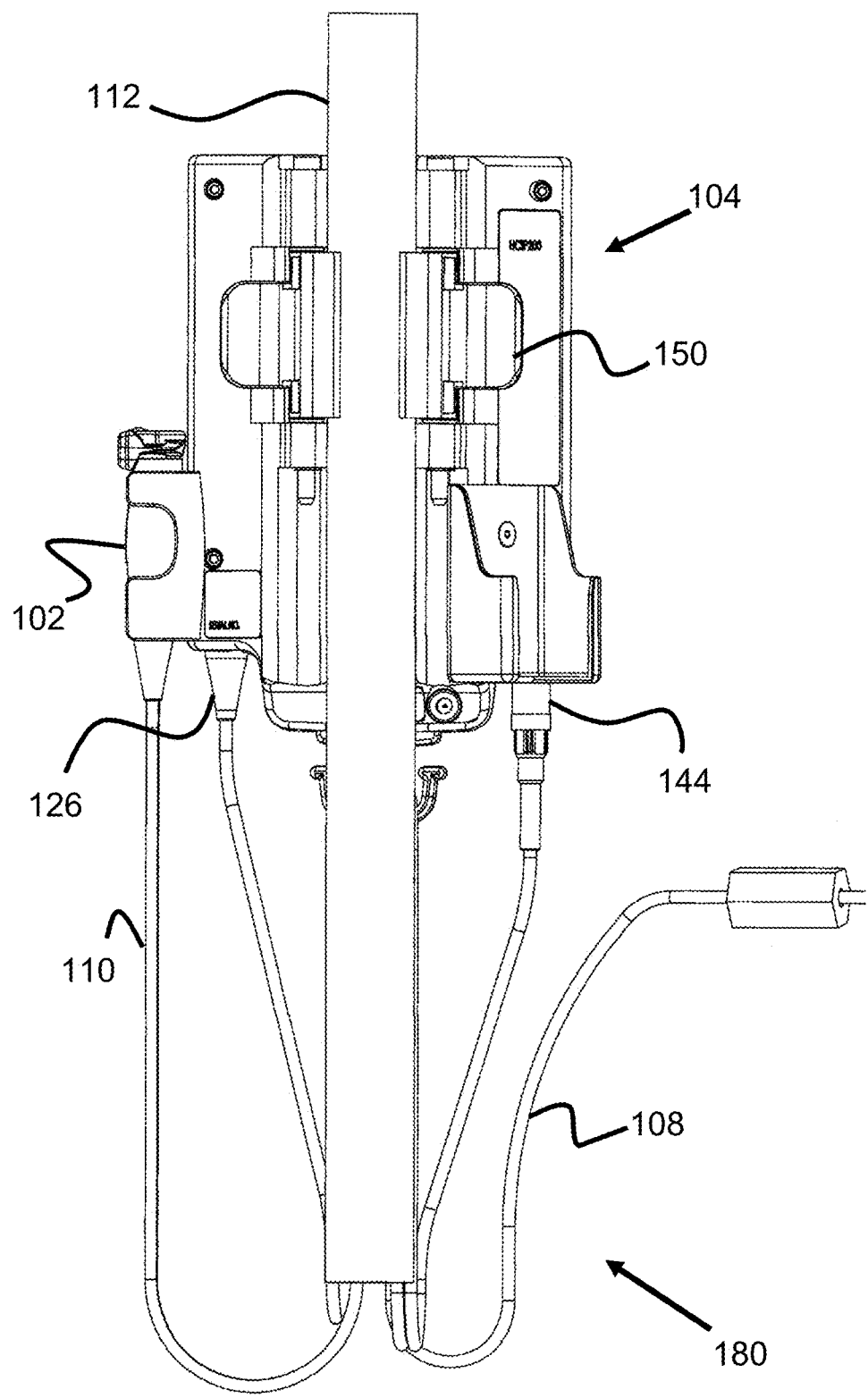
Figure 8:
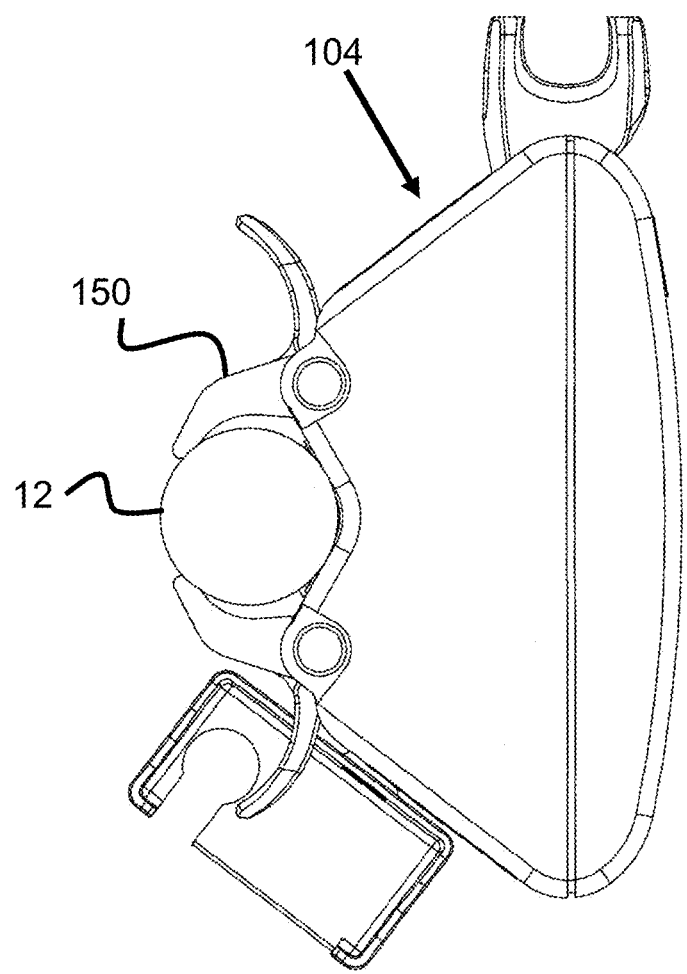
Figure 10:
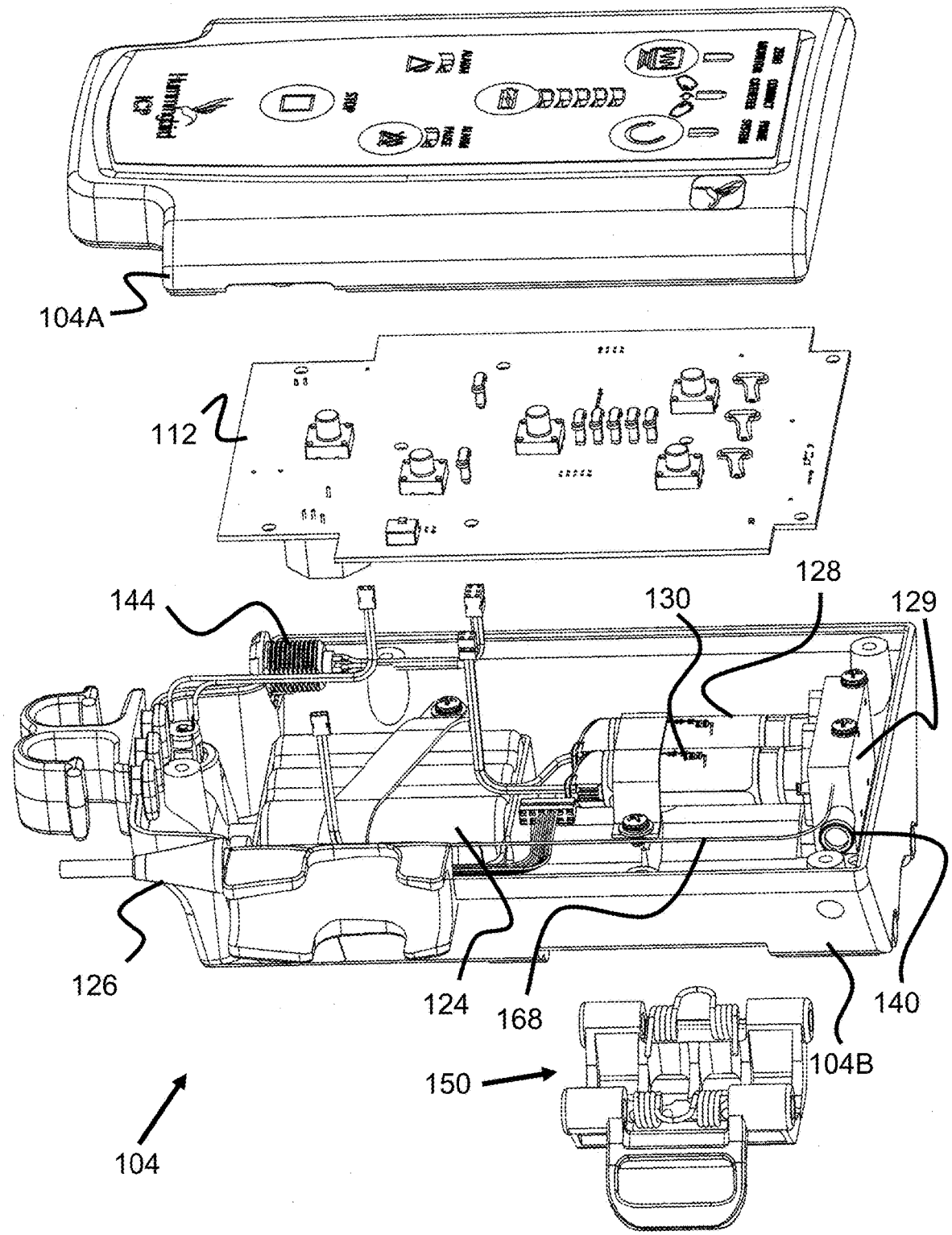

FIGS. 7 and 8 illustrate a back and top view of the pump assembly 104, including two pivoting clamp members 150 that engage the I.V. pole, locking the pump assembly 104 in place. Preferably, the back area of the pump assembly 104 and each of the clamp members 150 are curved so as to accommodate the diameter of the pole 12. The clamp members 150 can be biased to a closed state (e.g., with springs as seen in FIG. 10) and/or can be lockable in position to prevent the pump assembly 104 from falling off. The clamp members 150 preferably have a relatively soft, elastomer layer that faces the IV pole 12, thereby increasing the friction with the pole.

Figure 9:
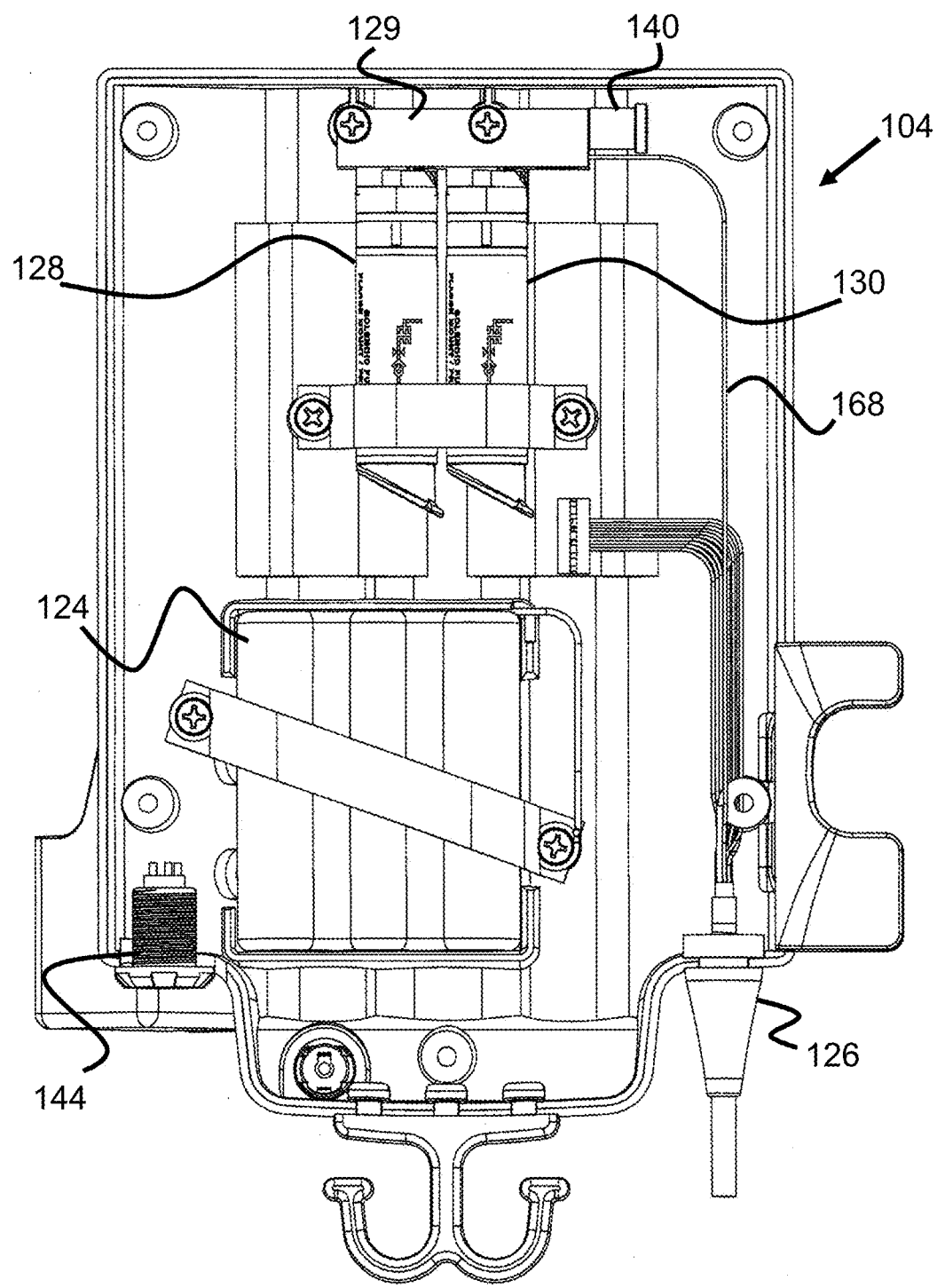
FIGS. 9 and 10 illustrate an interior of the pump assembly of FIG. 6A.

FIG. 9 illustrates a side view of the interior of the pump assembly 104 and FIG. 10 illustrates an exploded view of the assembly 104. The components of the pump assembly 104 are all contained within a front enclosure 104A and a back enclosure 104B. The circuit board 112 abuts the front enclosure 104A and preferably includes the button mechanisms and LEDs that are seen on the front user interface 146.

Beneath the circuit board 112, at the lower portion of the pump assembly 104 is the battery enclosure 124 that contains one or more batteries to power the pump assembly 104. Near the lower end of the enclosure 124 is a pair of wires that connect to the circuit board 112, providing it power.

Figure 11:
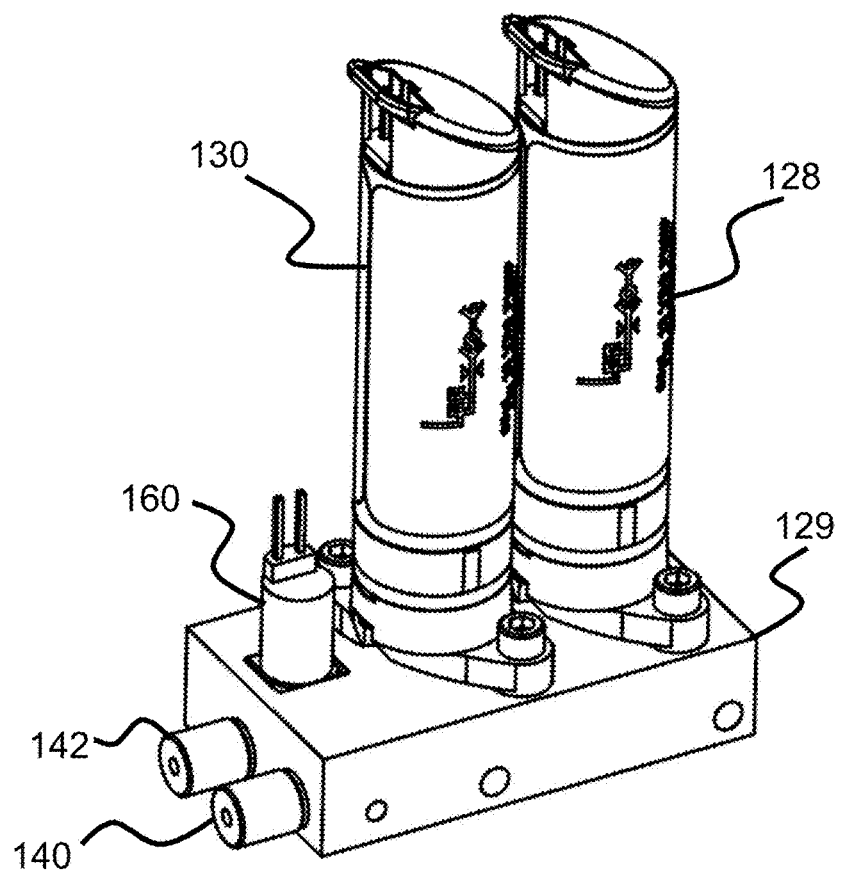
FIGS. 11 and 12 illustrate a pump manifold and pumps from FIG. 9.
Figure 12:
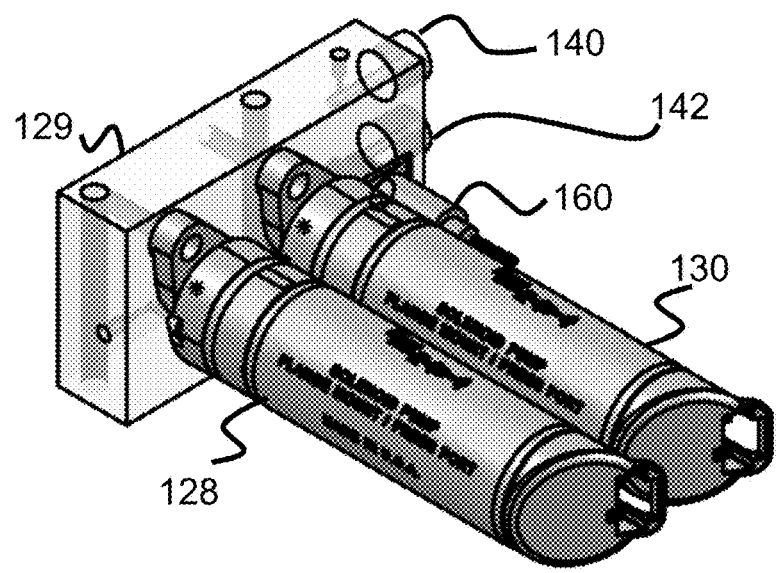

Beneath the circuit board 112, at the upper portion of the pump assembly 104 are solenoid pumps 128 and 130 (e.g., 50 µL or 65 µL pumps), which are connected to a pump manifold 129. FIGS. 11 and 12 illustrate these components in greater detail. The ports of the pumps 128, 130 both connect to a first internal manifold passage that connects to both the main air passage of the system (i.e., the passage connecting to the catheter 101) and to the output filter 142. A valve 160 opens or closes this first internal manifold passage to the filter 142 and therefore to the atmosphere within the pump assembly 104, thereby allowing the pumps to selectively discharge air to the atmosphere. The pump manifold also includes a second internal manifold passage that is connected to an air intake passage to the transducer assembly 102 (described later in this specification) and to the input filter 140, which allows air to flow from the pump assembly 104 to the transducer assembly 102.

As best seen in FIG. 10, the circuit board 112 is connected via wires to the pumps 128, 130 to allow for their actuation, to the transducer assembly connector 144 to provide power and receive the transducer data, and to monitor connector 126 to provide pressure data to the monitor.

Figure 13:
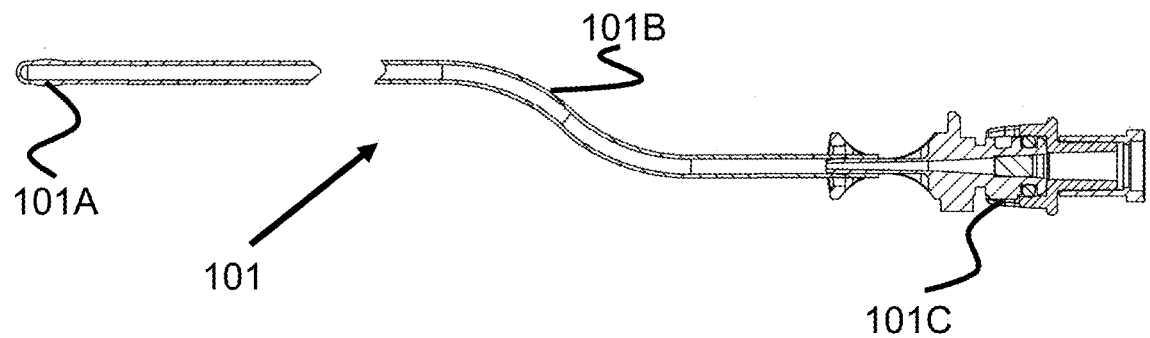
FIG. 13 illustrates an air catheter.

FIG. 13 illustrates an example air pressure catheter 101 having an air bladder 101A, a catheter tube 101B with an internal air passage, and a connector assembly 101C that connects with the connector assembly 152 of the transducer assembly 102.

Figures 14, 15:
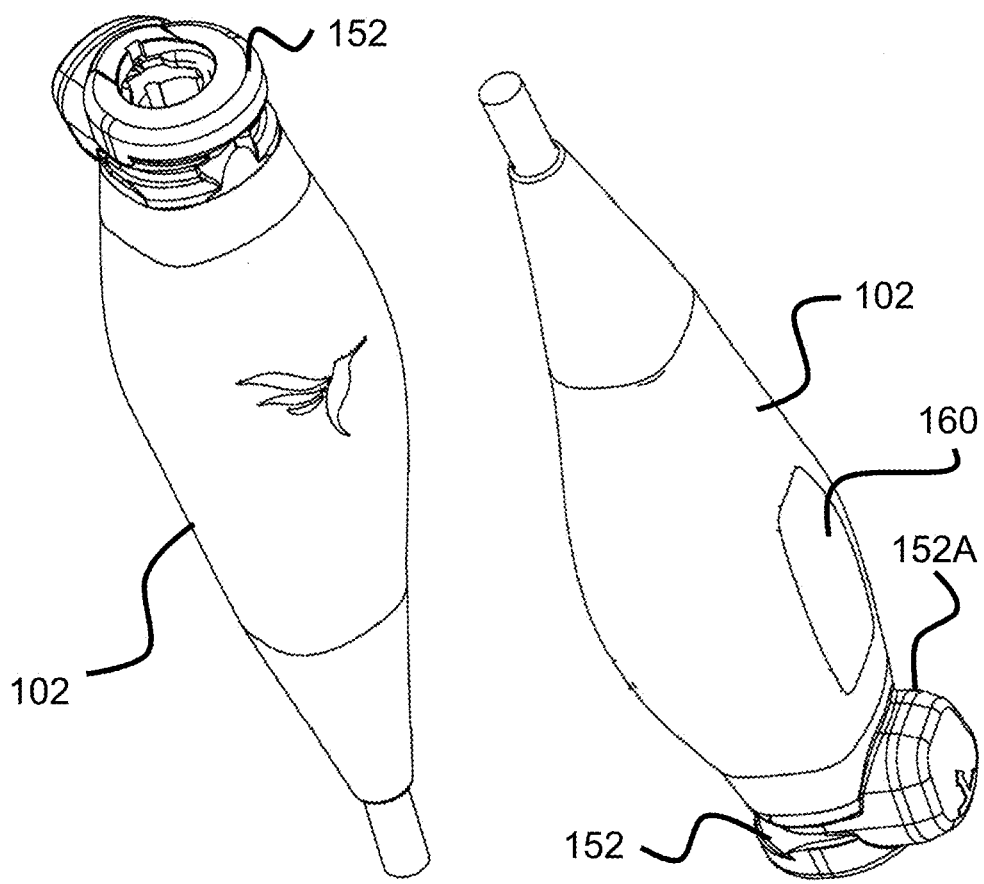
FIGS. 14 and 15 illustrate an outside view of a pressure transducer assembly.

FIGS. 14-19 illustrates various aspects of the pressure transducer assembly 102. As seen in FIG. 15, the assembly 102 includes an indicator 160 which includes one or more LEDs that indicate if the catheter 101 is properly connected. As seen best in FIGS. 16 and 17, the connector assembly 152 includes a biased latching mechanism 152B that maintains the catheter's connector assembly 101C in a locked configuration. A removable protective cover 152A is located over the latch 152B, thereby protecting from accidental disconnection of the catheter 101. Additional details of the connection mechanism can be found in U.S. patent Ser. No. 14/643,997, the contents of which are incorporated herein by reference.

Figure 16:
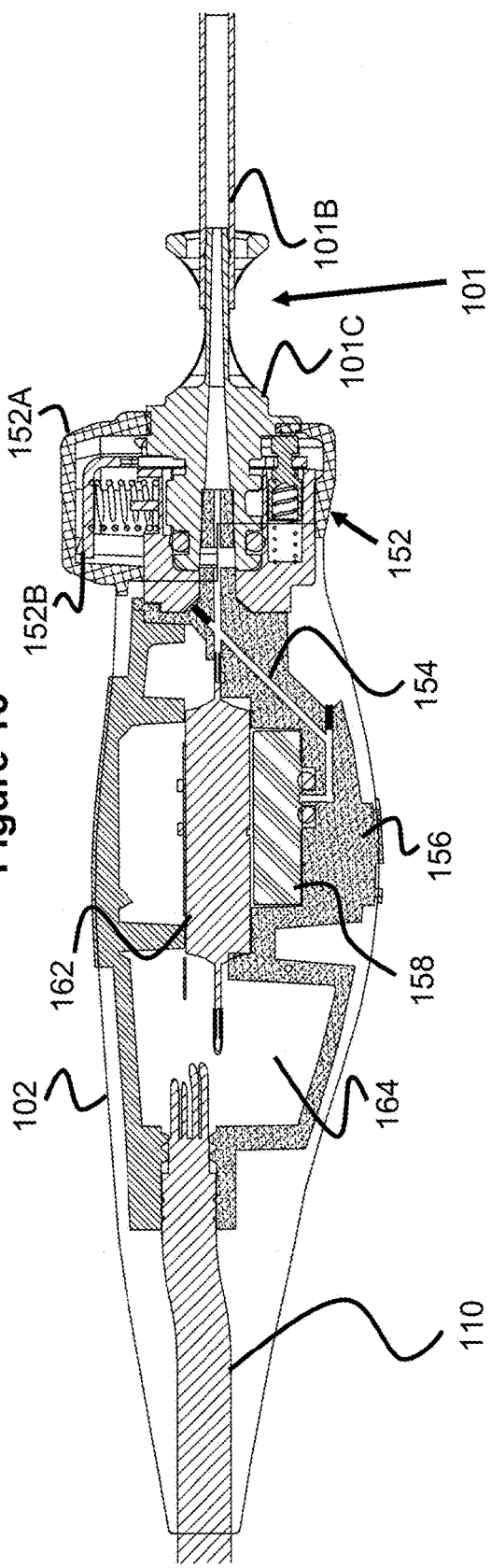
FIGS. 16-19 illustrate various views of an interior of the pressure transducer assembly of FIG. 14.
Figure 17:
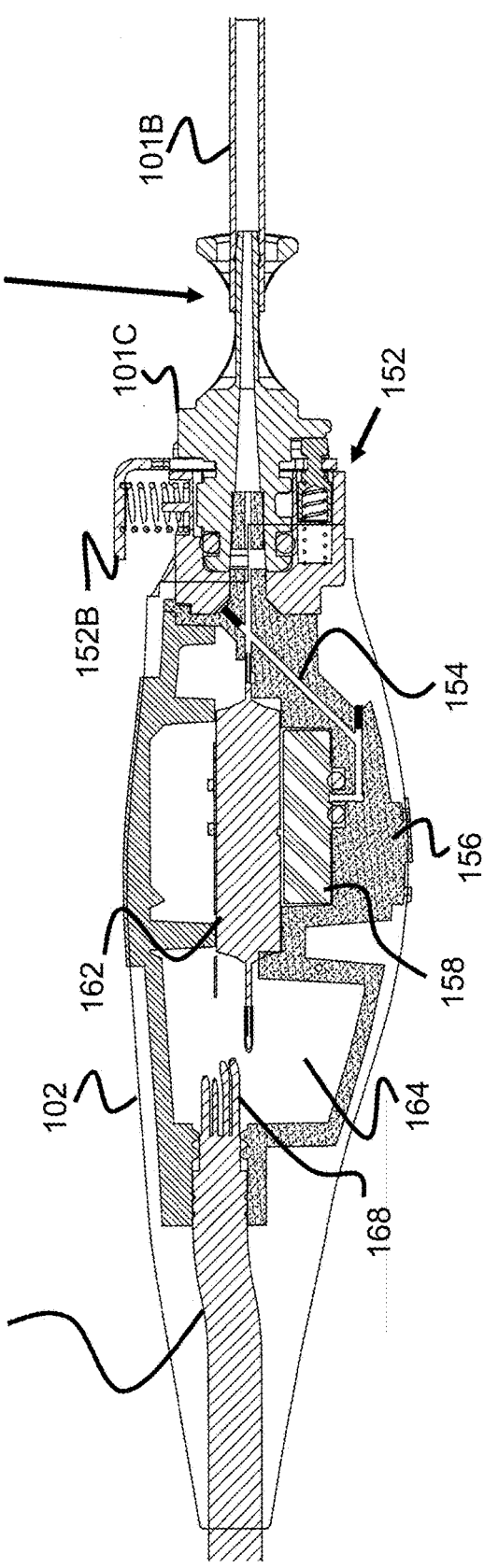
Figure 18:
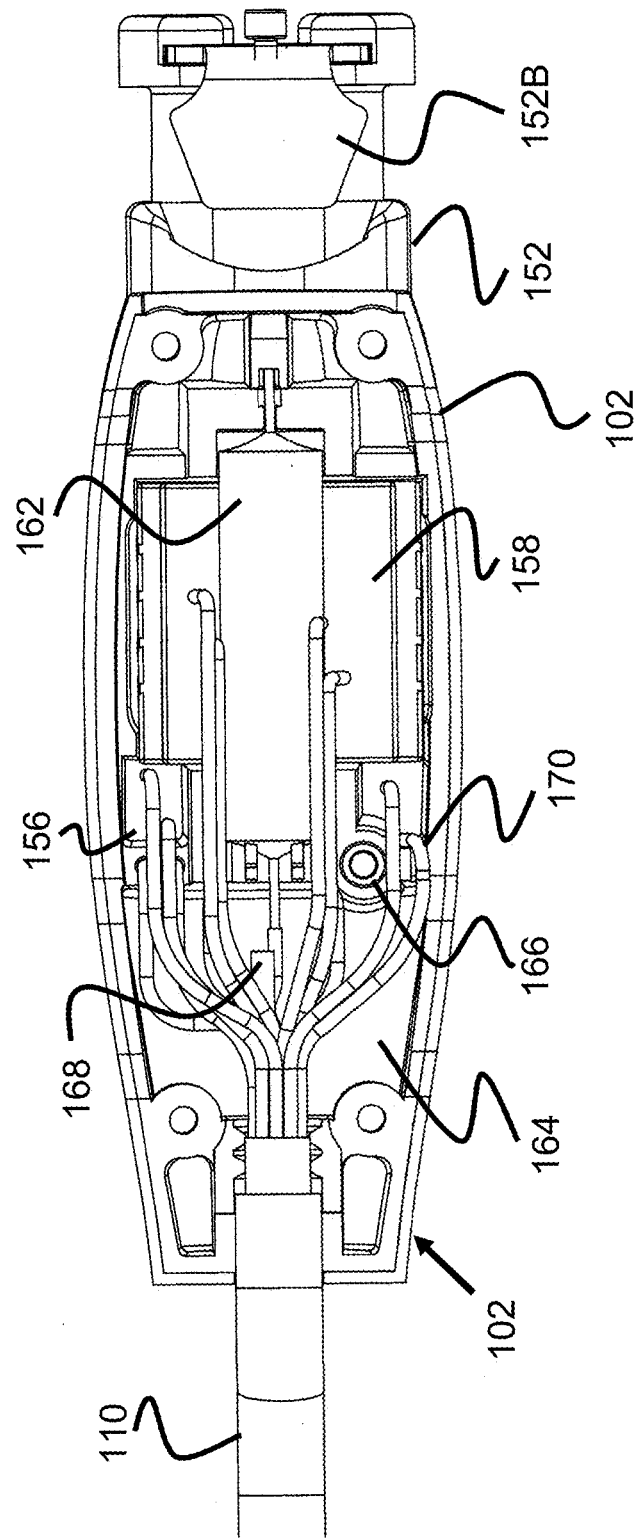
Figure 19:
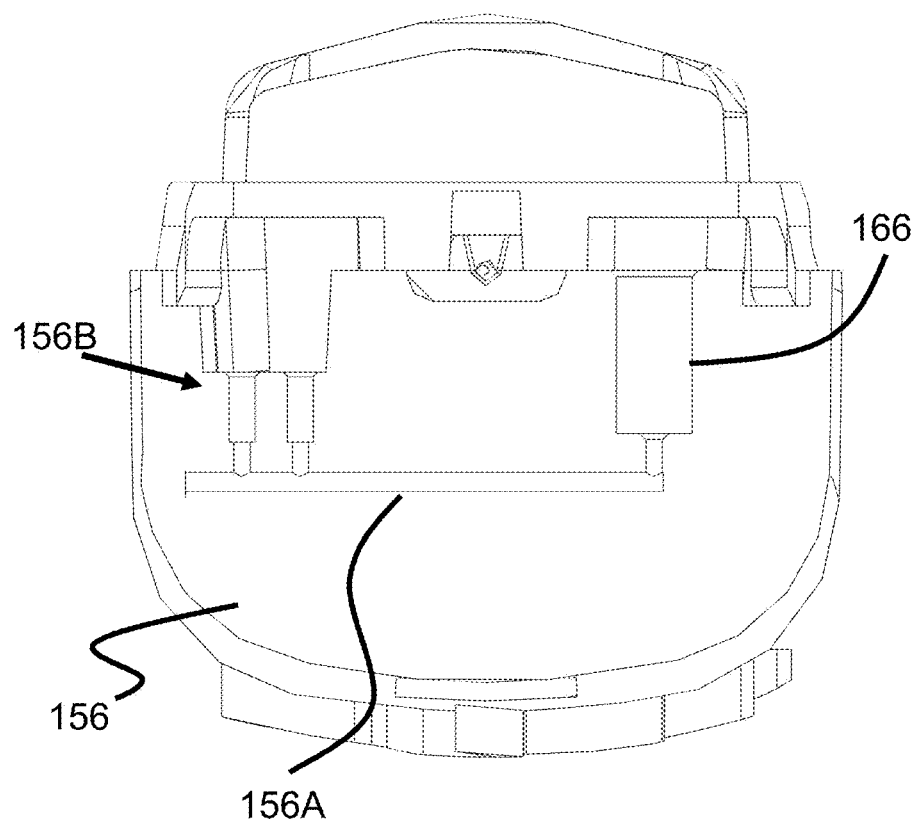

As best seen in FIGS. 16-18, the air passage of the catheter 101 continues through the passage 154 of the manifold 156, downwards, then up into a bottom port of the pressure transducer 158. Preferably, the diameter of the passage 154 is small, such as 0.0020", to help minimize the amount of the air passage volume and therefore provide optimal air volume within the catheter bladder at different external pressures and thereby offering more accurate pressure readings.

The passage within the transducer 158 then further connects with solenoid valve 162, which either closes off the tranducer's passage during operation, or opens up the passage during priming. The solenoid valve 162 is then connected to a manifold passage 156A within the manifold 156, best seen in FIG. 19. The passage 156A has two ports 1568 and a check valve 166. One of the ports 1568 is connected to the solenoid valve 162, while the other is connected to the pneumatic conduit in the cable 110 that leads to the pump assembly 104. In this respect, the passage 156A provides communication with the main air passage and the check valve 166.

When the check valve 166 is caused to be opened (e.g., at a predetermined negative pressure), it takes in air from within area 164. Area 164 is in communication with intake passage 168, which connects to the second passage in the pump manifold 129, which ultimately leads to the input filter 140. Hence, the area 164 is in communication with the atmosphere, allowing the check valve 166 to intake air.

As best seen in FIG. 18, in addition to the main air passage and the air intake passage, a plurality of electrical wires are also connected within the transducer assembly 102 for powering the valve 162, powering and communicating with the transducer 158, and powering the indicator 160.

Figure 20:
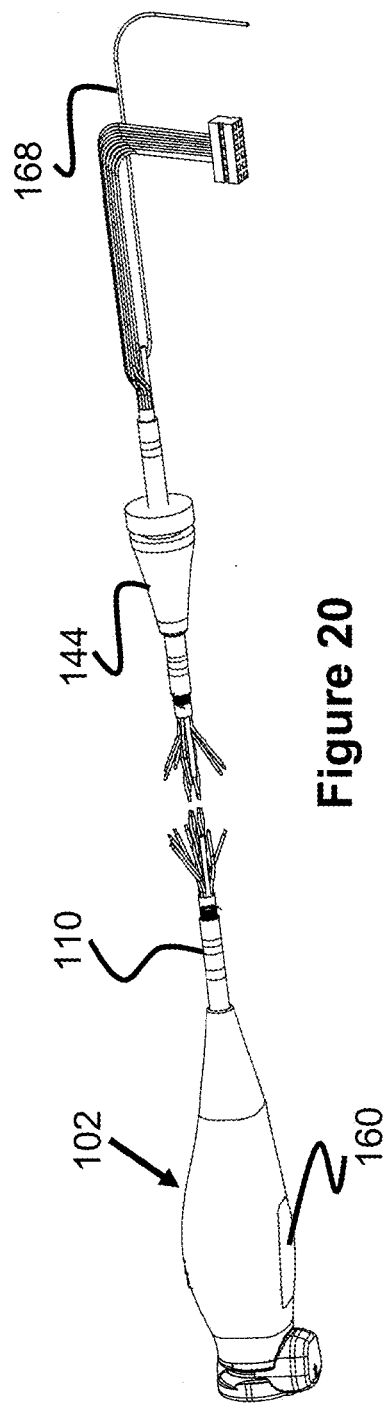
FIG. 20 illustrates a pressure transducer assembly and pressure transducer assembly cable.
Figure 21:
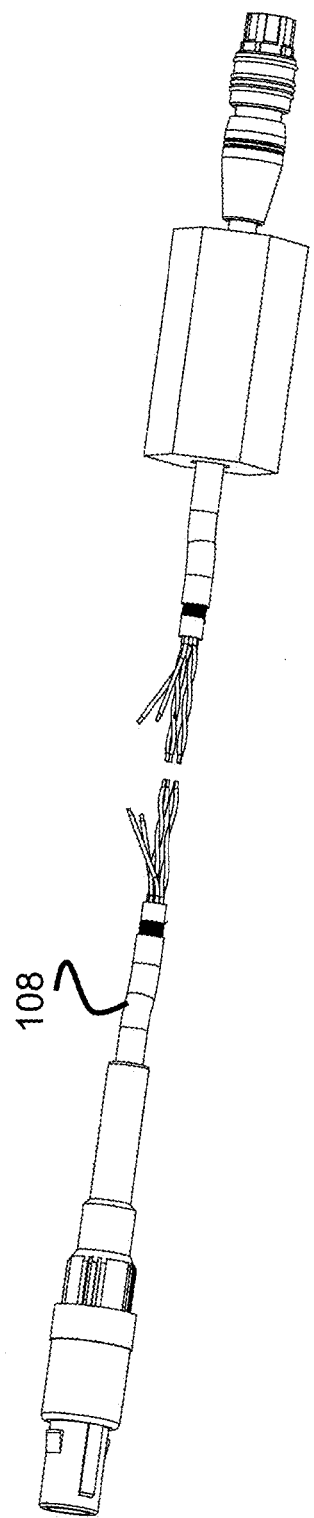
FIG. 21 illustrates a pressure monitor cable.

FIG. 20 illustrates another view of the pressure transducer assembly 102 and cable 110. FIG. 21 illustrates another view of the monitor cable 108.

Figure 22:
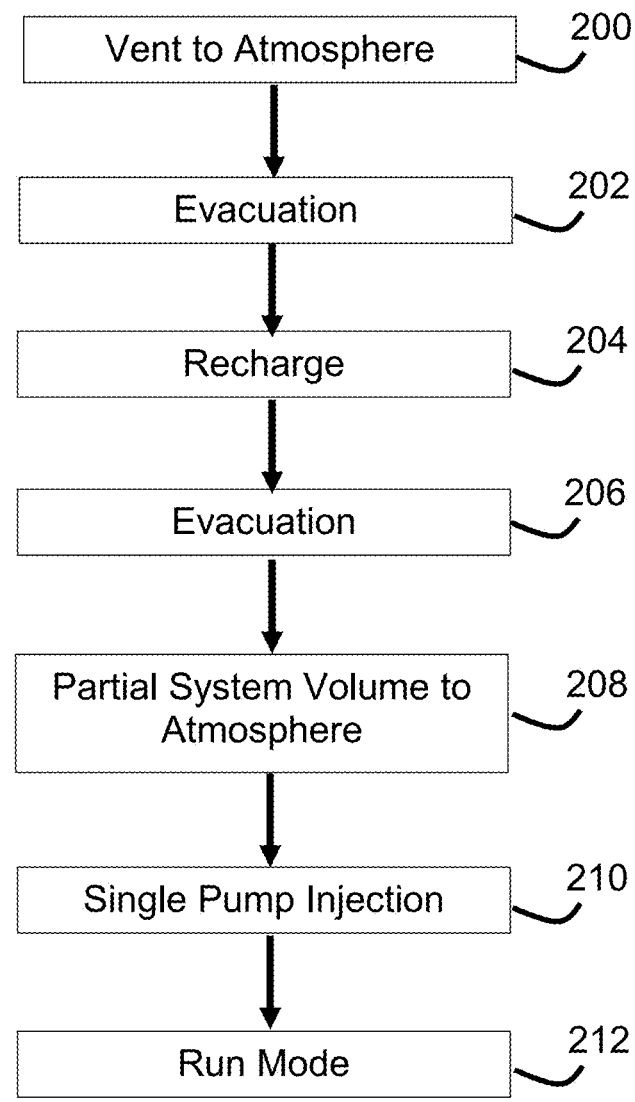
FIG. 22 illustrates a flow chart describing the process of priming the system with a specific amount of air.

FIG. 22 illustrates a flow chart for priming the previously discussed system 180. In step 200, the system vents to atmosphere. Specifically, valve 162 and valve 160 are both opened, allowing the entire main air passage to equalize with the atmospheric pressure.

In step 202, evacuation occurs. First, valve 160 is closed (valve 162 remains open). Next, solenoid pumps 128, 130 are activated so as to increase the overall volume in the system (i.e., suck out some of the air from the main air passage). Finally, valve 162 is closed, isolating the passage 154 and the passage within the catheter 101.

In step 204, recharging occurs. First, valve 160 is opened and the pumps 128, 130 are activated so as to decrease the overall volume, pushing air out via filter 142. Valve 160 is then closed to seal off the main air passage.

In step 206, evacuation occurs again. First, valve 160 is closed (valve 162 remains open). Next, solenoid pumps 128, 130 are activated so as to increase the overall volume in the system (i.e., suck out some of the air from the main air passage). Finally, valve 162 is closed, isolating the passage 154 and the passage within the catheter 101. If the negative air pressure in the main air pressure passage exceeds the crack pressure of the check valve 166 (such as a pressure between 40-60 mmHg), the check valve 166 will open, taking in air from area 164, until the air pressure within the main air passage reaches that crack pressure and the valve 166 closes. At this time, the pump assembly 104 monitors the pressure in the main air passage to determine if it indeed reached the desired level of the crack pressure of the valve. If not, the evacuation step is performed again.

Once the desired pressure has been achieved (i.e., the crack pressure of check valve 166), a partial system volume to atmosphere step 208 is performed. Valve 160 is opened (valve 162 remains closed) while only solenoid pump 128 is activated so as to increase the overall volume in the main air passage. Next, valve 160 is closed, closing off communication with the input filter 142.

In step 210, a single pump injection is performed. First, valve 162 is opened, allowing access to passage 154 and to the air passage of the catheter 101. Next, the pump 128 is activated so as to decrease the volume in the main air passage, thereby injecting additional air into the system.

Finally, in the run mode step 212, the valve 162 is closed, isolating the transducer 158, the passage 154, and the passage within the catheter 101. At this time, the volume of air and pressure in the passage is known. As the pressure within the patient (e.g., within the cranium of the patient) pushes on the flexible bladder 101A of the catheter 101, the pressure within the patient can also be calculated according to Boyle's Law ($P_1V_1=P_2V_2$).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An automatic air pressure management system for monitoring intra-cranial pressure within a patient with an air catheter, comprising:
   an air pump mechanism configured to pump air into the air catheter, where the air catheter is configured to be located within the cranium of the patient;
   a control assembly;
   a pressure transducer;
   a first valve opening to the atmosphere outside of said automatic air pressure management system; an air catheter connection mechanism that releasably connects to said air catheter;
   a common air passage in communication with said air pump mechanism, said pressure transducer, said first valve, and said air catheter connection mechanism;
   and, a second valve selectively isolating said pressure transducer and said air catheter connection mechanism from said air pump mechanism and said first valve within said common air passage;
   wherein said control assembly is configured to actuate the actions below in the following order:
   activate said pump mechanism to evacuate air from said common air passage with said first valve being closed and said second valve being open;
   close said second valve so as to isolate said pressure transducer and said air catheter connection mechanism;
   open said first valve to inject air into said common air passage;
   close said first valve; and,
   open said second valve to inject air to an air catheter attached to said air catheter connection mechanism to achieve a predetermined pressure.

2. The automatic air pressure management system of claim 1, wherein said air pump mechanism, said control assembly, and said first valve are located in a pump assembly enclosure, and wherein said pressure transducer, said air catheter connection mechanism, and said second valve are located in a pressure transducer assembly enclosure.

3. The automatic air pressure management system of claim 1, wherein said air pump mechanism further comprises a first pump and a second pump.

4. The automatic air pressure management system of claim 1, wherein said control assembly is further configured to measure an air pressure with said pressure transducer.

5. The automatic air pressure management system of claim 2, further comprising a pressure transducer assembly cable connecting said pump assembly enclosure with said pressure transducer assembly enclosure.

6. The automatic air pressure management system of claim 1, wherein said control assembly is further configured to vent said common air passage, evacuate air from said common air passage by activating said pump mechanism, and open said first valve to allow air into said common air passage.

7. The automatic air pressure management system of claim 1, further comprising a monitor connection socket that is connectable with a pressure monitor cord to a pressure monitor.

8. The automatic air pressure management system of claim 1, further comprising a check valve connected to said common air passage and allowing air to enter said common air passage when a pressure differential between said common air passage and ambient air pressure outside of said automatic air pressure management system is greater than a crack pressure of said check valve.

* * * * *